(12) United States Patent
Hajnal et al.

(10) Patent No.: US 8,842,896 B2
(45) Date of Patent: Sep. 23, 2014

(54) IMAGING OF MOVING OBJECTS

(75) Inventors: Joseph Vilmos Hajnal, London (GB); Shuzhou Jiang, Causeway Bay (GB)

(73) Assignee: Imperial Innovations Limited, London (GB)

( * ) Notice: Subject to any disclaimer, the term of this patent is extended or adjusted under 35 U.S.C. 154(b) by 668 days.

(21) Appl. No.: 12/598,845

(22) PCT Filed: May 2, 2008

(86) PCT No.: PCT/GB2008/001538
§ 371 (c)(1),
(2), (4) Date: Sep. 1, 2010

(87) PCT Pub. No.: WO2008/135741
PCT Pub. Date: Nov. 13, 2008

(65) Prior Publication Data
US 2010/0329528 A1   Dec. 30, 2010

(30) Foreign Application Priority Data

May 4, 2007   (GB) .................................. 0708655.6

(51) Int. Cl.
*G06K 9/00* (2006.01)
*A61B 5/055* (2006.01)
*G01R 33/565* (2006.01)
*G01R 33/563* (2006.01)
*G01R 33/567* (2006.01)

(52) U.S. Cl.
CPC .......... *G01R 33/56341* (2013.01); *A61B 5/055* (2013.01); *G01R 33/56358* (2013.01); *G01R 33/56509* (2013.01); *G01R 33/5676* (2013.01)
USPC ....................................................... 382/131

(58) Field of Classification Search
USPC .......................... 382/128–134; 128/920–925;
356/39–49; 600/407–414, 424–426;
345/581–618
See application file for complete search history.

(56) References Cited

U.S. PATENT DOCUMENTS

2005/0237057 A1   10/2005   Porter
2008/0097187 A1 *  4/2008   Gielen et al. .................. 600/409
2008/0253639 A1 * 10/2008   Van Den Brink ............. 382/131

FOREIGN PATENT DOCUMENTS

JP           2004-329269 A      11/2004

OTHER PUBLICATIONS

Jiang S. et al: "A Novel Approach to Accurate 3D High Resolution and High SNR Fetal Brain Imaging"; Hounsfield Lecture 2006, Imperial College, London, Research Poster Competition, [Online] Feb. 23, 2006, XP002493404; London, UK; Retrieved from the Internet:     URL:http://ubimon.doc.ic.ac.uk/isc/public/HPosters06 151-200/paper163.pdf>; [retrieved on Aug. 25, 2008].

(Continued)

*Primary Examiner* — Atiba O Fitzpatrick
(74) *Attorney, Agent, or Firm* — Fraser Clemens Martin & Miller LLC; William J. Clemens

(57) ABSTRACT

A method of generating an image data set, describing an object, as the object moves in a scanning space, comprises: a) performing a plurality of scans of the scanning space each scan being arranged to generate a set of samples, each sample including a sample value of at least one parameter associated with a respective point in the scanning space, the plurality of scans generating sample sets relating to a plurality of different parameters; b) determining a mapping for each of the samples from the scanning space into an object space which is fixed relative to the object; and c) determining object space values for each of the parameters at each of a plurality of points in the object space.

15 Claims, 10 Drawing Sheets

(56) References Cited

OTHER PUBLICATIONS

Shuzhou Jiang et al: "In-utero three dimension high resolution fetal brain diffusion tensor imaging"; Proceedings 10th International Conference Medical Image Computing and Computer-Assisted Intervention—MICCAI 2007, Part I. (Lecture Notes in Computer Science vol. 4791) Springer-Verlag Berlin, Germany, vol. pt. 1, Oct. 29, 2007, pp. 18-26, XP002493405; ISBN: 3-540-75756-2; the whole document.

Tony Bui et al: "Microstructural development of human brain assessed in utero by diffusion tensor imaging"; Pediatric Radiology, Springer, Berlin, DE, vol. 36, No. 11, Sep. 8, 2006, pp. 1133-1140, XP019458583; ISSN: 1432-1998; cited in the application; the whole document.

* cited by examiner

|  | RX (deg) | RY (deg) | RZ (deg) | TX (mm) | TY (mm) | TZ (mm) |
|---|---|---|---|---|---|---|
| Mean absolute Difference | 0.505 | 0.297 | 0.184 | 0.214 | 0.562 | 0.810 |
| STD absolute Difference | 0.487 | 0.207 | 0.106 | 0.191 | 0.512 | 0.642 |

TABLE I

Fig. 8

| | SCC | | PLIC | | FC | | GCC | | ALIC | | PCR | | SLF | | SCR | |
|---|---|---|---|---|---|---|---|---|---|---|---|---|---|---|---|---|
| | Mean ADC | STD ADC | Mean ADC | STD ADC | Mean ADC | STD ADC | Mean ADC | STD ADC | Mean ADC | STD ADC | Mean ADC | STD ADC | Mean ADC | STD ADC | Mean ADC | STD ADC |
| Reconstructed | 0.75 | 0.05 | 0.88 | 0.09 | 0.88 | 0.09 | 0.89 | 0.09 | 0.80 | 0.07 | 0.86 | 0.04 | 0.81 | 0.06 | 0.84 | 0.05 |
| Gold Standard | 0.78 | 0.11 | 0.91 | 0.06 | 0.88 | 0.09 | 0.91 | 0.1 | 0.83 | 0.08 | 0.89 | 0.04 | 0.83 | 0.05 | 0.86 | 0.04 |
| | Mean nFA | STD FA | Mean nFA | STD FA | Mean nFA | STD FA | Mean FA | STD FA | Mean FA | STD FA | Mean nFA | STD FA | Mean nFA | STD FA | Mean nFA | STD FA |
| Reconstructed | 0.74 | 0.11 | 0.64 | 0.04 | 0.56 | 0.09 | 0.65 | 0.09 | 0.56 | 0.07 | 0.56 | 0.09 | 0.52 | 0.10 | 0.42 | 0.07 |
| Gold Standard | 0.75 | 0.11 | 0.63 | 0.04 | 0.57 | 0.11 | 0.63 | 0.07 | 0.56 | 0.09 | 0.58 | 0.11 | 0.53 | 0.10 | 0.42 | 0.04 |

TABLE 2

TABLE 3

Fig. 11

IMAGING OF MOVING OBJECTS

FIELD OF THE INVENTION

The present invention relates to imaging, and in particular medical imaging. More specifically it relates to the imaging of objects that are moving.

BACKGROUND TO THE INVENTION

Imaging of moving objects (eg: organs in the chest and abdomen, the heart, moving joints) is of increasing clinical and medical research interest. A common solution to this problem is to acquire multiple sets of motion-frozen images, each of which is reasonably motion-free, but which taken together do not form part of a consistent representation of the subject. For diagnostic purposes, these motion-frozen components may be sufficient, but for quantitative analysis (eg: measuring structure volumes, or tissue function), it is necessary to generate a geometrically consistent set of data from all the motion-frozen images in order to obtain reliable measurements of the quantitative parameters. This applies, for example, to medical imaging modalities including MRI, CT, PET, SPECT and ultrasound. For MRI, the imaging might be from one of the many methods that require multiple correctly aligned measurements in order to derive the quantitative parameters e.g: diffusion imaging (DWI or DTI), functional MRI (BOLD fMRI), MRI relaxometry (e.g: $T2^*$ quantification from iron oxide contrast agents).

An especially challenging task is Foetal brain imaging by MRI which is attracting increasing interest because it offers excellent contrast and anatomical detail. However, unpredictable foetal motion has led to the widespread use of single shot techniques that can freeze foetal motion for individual slices. This provides high quality anatomical slices but these are generally inconsistent with one another. We previously developed a method, Snapshot images with Volume Reconstruction (SVR), for three dimensional (3D) high resolution and high SNR in-utero anatomical imaging of the foetal brain using dynamic scanning and image registration (see refs. 1-3). Fine structure of the in-utero foetal brain is clearly revealed for the first time at millimetric resolution from all three dimensions and substantial SNR improvement is realized by having many individually acquired slices contribute to each voxel in the reconstructed image.

An even greater challenge is in-utero Diffusion Weighted Imaging (DWI). It is highly sensitive in detecting certain brain diseases such as hypoxic-ischemia or periventricular leukomalacia (see refs. 4, 5) as well as for observing normal cerebral development. Preliminary trials (see ref. 6) have been performed in which for a few relatively thick slices, a b=0 (reference) together with 3 directions of diffusion weighted images were acquired within a maternal breath hold time, e.g. 20 seconds. These early experiments relied on the chance event of the foetus remaining still for all 4 sets of images so that apparent diffusion coefficients (ADC) could be calculated.

Diffusion tensor imaging (DTI) offers the potential for More information than DWI, and has been widely used in both adult (7) and neonatal studies(8, 9), particularly for tractography studies. However, DTI is even more challenging than DWI for foetal imaging, because it requires a b=0 image and at least 6 diffusion images that are sensitized in non-colinear directions for each slice studied. These extra images increase the minimum acquisition time so that the requirements for the maternal breath-hold become more onerous. Without a maternal breath-hold foetal motion combines with the mother's respiration to disrupt the spatial correspondence between component images required to calculate tensor properties. Moreover, the added diffusion sensitizing gradients make the diffusion weighted images highly sensitive to even small amount of motion. This results in data that is frequently corrupted by in-plane motion as well. Very recently, Bui et al (see ref. 10) reported diffusion tensor imaging with 6 non-colinear directions with in-plane resolution is 2.95 mm×1.09 mm, and 5 mm slice thickness. The whole sequence took 53 second and the mother was sedated. Besides the ADC value, they measured some Fractional Anisotropy (FA) values but without showing any FA maps.

The challenge of imaging subjects that cannot remain sufficiently still for conventional methods to be applicable is much more widespread than foetal imaging and includes subjects such as babies or children who may not be able to remain still and categories of patients who are unable to follow instructions or are subject to uncontrollable movements. Likewise the methods proposed are applicable to any other imaging protocol that requires multiple measurements to be combined. Example include functional Magnetic Resonance Imaging (fMRI), perfusion imaging, dynamic contrast imaging, magnetization transfer imaging, quantitative T1 or T2 imaging, temperature imaging and elastography as well as other modalities such as CT, PET and ultrasound.

SUMMARY OF THE INVENTION

The present invention provides a method of generating an image data set, describing an object, as the object moves in a scanning space relative to a scanner, the method comprising: a) performing a plurality of scans of the scanning space each scan being arranged to generate a set of samples, each sample including a sample value of at least one parameter associated with a respective point in the scanning space, the plurality of scans generating sample sets relating to a plurality of different parameters; b) determining a mapping for each of the samples from the scanning space into an object space which is fixed relative to the object; and c) determining object space values for each of the parameters at each of a plurality of points in the object space.

If the scanning space is considered to be defined by the scanner, then movement of the object while the scanner is stationary, or movement of the scanner while the object is stationary, or indeed movement of both scanner and object, will result in movement of the object relative to the scanner and relative to the scanner space.

The scan may be of many different types, in particular tomographic scans, including for example magnetic resonance imaging (MRI), functional MRI (fMRI), ultrasound, relaxometry, elastography, contrast uptake, magnetisation transfer imaging, temperature mapping and perfusion imaging, and also other modalities including ultrasound (multiple 2D or 3D images from different transducer positions), CT imaging of moving objects or for functional measurements such as perfusion, PET-CT imaging where the PET and CT image are acquired at separate times but require integration. The parameter will therefore depend on the type of scan. For example for MR relaxometry the parameter may be, or be indicative of, a relaxation time. For fMRI the parameter may be, or may be indicative of, magnetic susceptibility.

The different sampled parameters may have different control parameters associated with them. For example in diffusion weighted MRI scanning, the different control parameters may be the different diffusion directions and the different sampled parameters may be the diffusion weighting coefficients in those different directions. Alternatively the different sampled parameters may have different state parameters associated with them. For example in fMRI scans where a subject is scanned in different states, the different sampled parameters would be pixel intensity values for the same pixel when the subject is in the different states.

The points in object space may be arranged in a regular grid. The object space values may be determined by interpolation from the samples after the samples have been mapped into the object space. This is because the mapped samples will, in general, be irregularly spaced, or scattered, within the object space.

Each of the values may have a direction associated with it and the mapping may include a rotation for each of the samples. For example if the scans are diffusion weighted MRI scans the values may be diffusion weighted coefficients.

The object space values may be determined from the samples and the mapping using a linear process, such as a matrix equation, defining the relationship between the object space values, the mapping, and the samples. Where the samples are values of sample parameters having different control or state parameters associated with them, the object space values may be determined from any one or more of the sample values, the sample parameters, the control or state parameters, and the mapping. Preferably all of the sample data for an image is input into a single matrix equation which can be used to generate a complete image data set from all of the sample values for all of the parameters.

The step of determining a mapping may comprise registration of each of the sample sets with a reference data set. For example each of the scans may be arranged to scan a plurality of slices of the scanner space, and each of the sample sets may comprise a plurality of sample slices each sample slice comprising a plurality of samples and being associated with one of the slices of scanner space. Each slice or group of slices is preferably acquired over a timescale small enough so that the object can be assumed to be stationary during the acquisition of the slice or group of slices. However movement of the object between acquisition of the slices or groups of slices is accounted for in the mapping.

The present invention further comprises a method of generating an image of an object, the method comprising generating an image data set according to the method of the invention and generating an image from the data set.

The present invention still further provides a system for producing an image data set describing an object, the system comprising an input arranged to receive a plurality of sets of samples, each sample including a sample value of at least one parameter associated with a respective point in a scanning space, the sets relating to a plurality of different parameters; and processing means arranged to: determining a mapping for each of the samples from the scanning space into an object space which is fixed relative to the object; and determine object space values for each of the parameters at each of a plurality of points in the object space.

The present invention further provides a system for producing a dynamic image comprising a system according to the invention and a display, wherein the processing means is arranged to control the display to produce a display from the image data set. The system may further comprise a scanner arranged to generate the sets of sample data.

The present invention further provides a data carrier carrying data arranged when run on a computer to make it perform the method of the invention.

The present invention extends the SVR technique so that it can be used, for example, in diffusion tensor imaging (DTI) of the in-utero foetal brain. To achieve high resolution in all three dimensions for both non-diffusion and diffusion weighted images of the foetal brain we have developed a complementary approach that uses dynamic EPI scanning without/with added diffusion gradient to sample the spatial region containing the brain with multiple overlapping slices. Repeated sampling of slice planes makes it highly probable that every part of the foetal brain is sampled on a set of images that contain both non-diffusion images and diffusion weighted images from at least 6 independent diffusion gradient directions even when there is significant motion. Image registration is then used to retrospectively align the images obtained based on the assumption that they represent a single rigid body undergoing an unknown motion. Having determined the correct location of each image in a self consistent anatomical space of the foetal brain, a 3D b=0 volume is first reconstructed using the scattered data interpolation method described in the SVR method (see ref. 3). Alternatively least squares regression can be used to reconstitute the b=0 volume. Then, we regard the measured voxel intensities from all the diffusion weighted slices as valid samples at known although irregularly spaced locations and under known diffusion gradient direction, and use the Least Squares Regression (LSQR) method (see ref. 11) or other suitable algorithm to reconstruct an optimal estimate of the 3×3 symmetrical diffusion tensor matrix for every voxel of the 3D foetal brain on a regular Cartesian voxel lattice. The estimated distribution of diffusion tensors can be used to assist the in the registration process by providing a forward model of the intensities in each individual diffusion weighted image taking into account the current best estimate of location and orientation of the direction of diffusion sensitization implied by this location. Once refined estimates of the positions of all the slices have been achieved, a new reconstruction of the diffusion tensors can then be made.

Although having particular application in foetal scanning, the present invention has wide application to perform diffusing tensor imaging and other types of multi-parameter imaging on moving objects that can be assumed to have a constant shape, particularly when there may be other objects in the field of view that undergo differential motion and/or changes in shape. We have therefore tested the method in the general context of imaging the brains of subjects who cannot remain sufficiently still for conventional DTI examinations and used the method for other parameter map estimation such as in fMRI.

Preferred embodiments of the invention will now be described by way of example only with reference to the accompanying drawings.

BRIEF DESCRIPTION OF THE DRAWINGS

FIG. 8 is Table 1 that shows the difference in registration accuracy between the slice-to-volume and the gold standard volume-to-volume registration using Image Registration Toolkit. 819 individual slices are tested in total.

FIG. 9 is Table 2 that shows eight Region of Interest (ROI) Measurement on ADC and FA values for Both Reconstructed Motion Data and Gold Standard Still Data.

Figure 10:
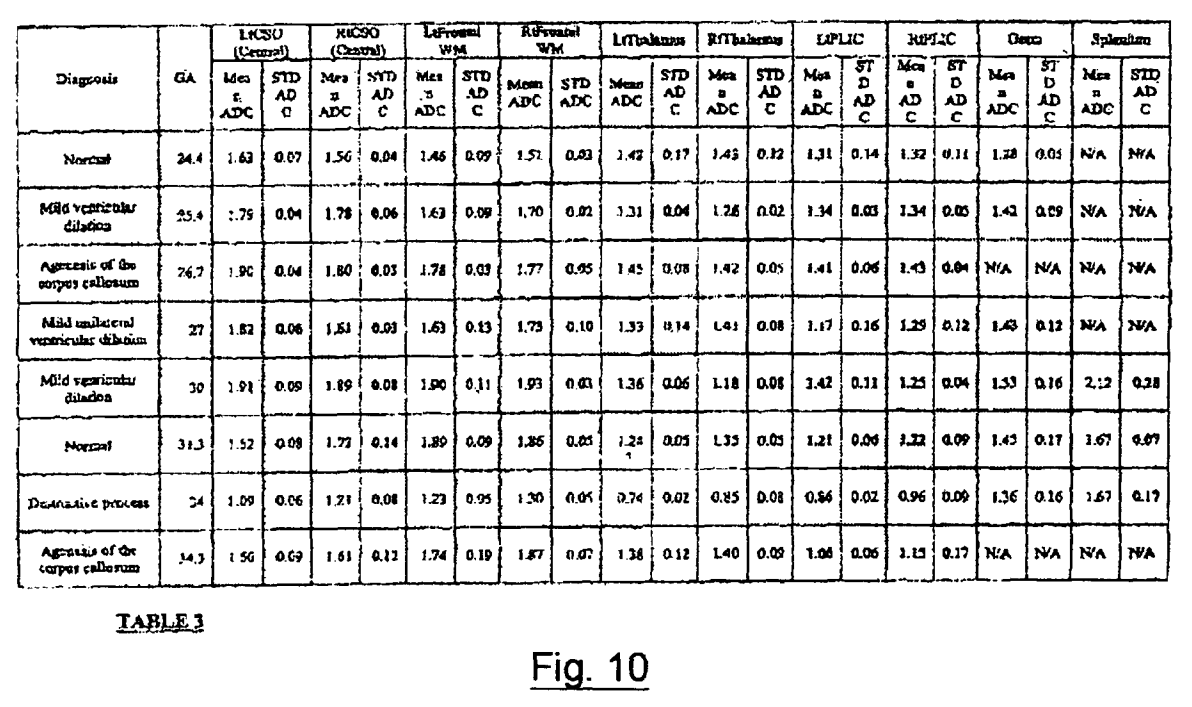

FIG. 10 is Table 3 that shows ten Region of Interest (ROI) Measurement on ADC values for eight *in-utero* foetal subjects.

Figure 11:
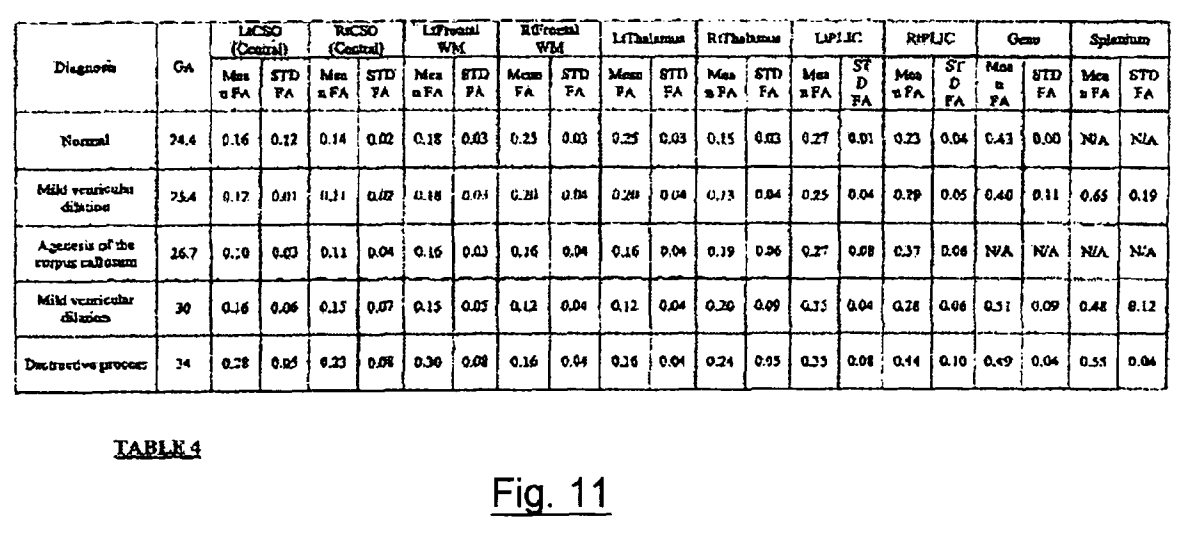

FIG. 11 is Table 4 that shows ten Region of Interest (ROI) Measurement on FA values for five *in-utero* foetal subjects.

Figure 1:
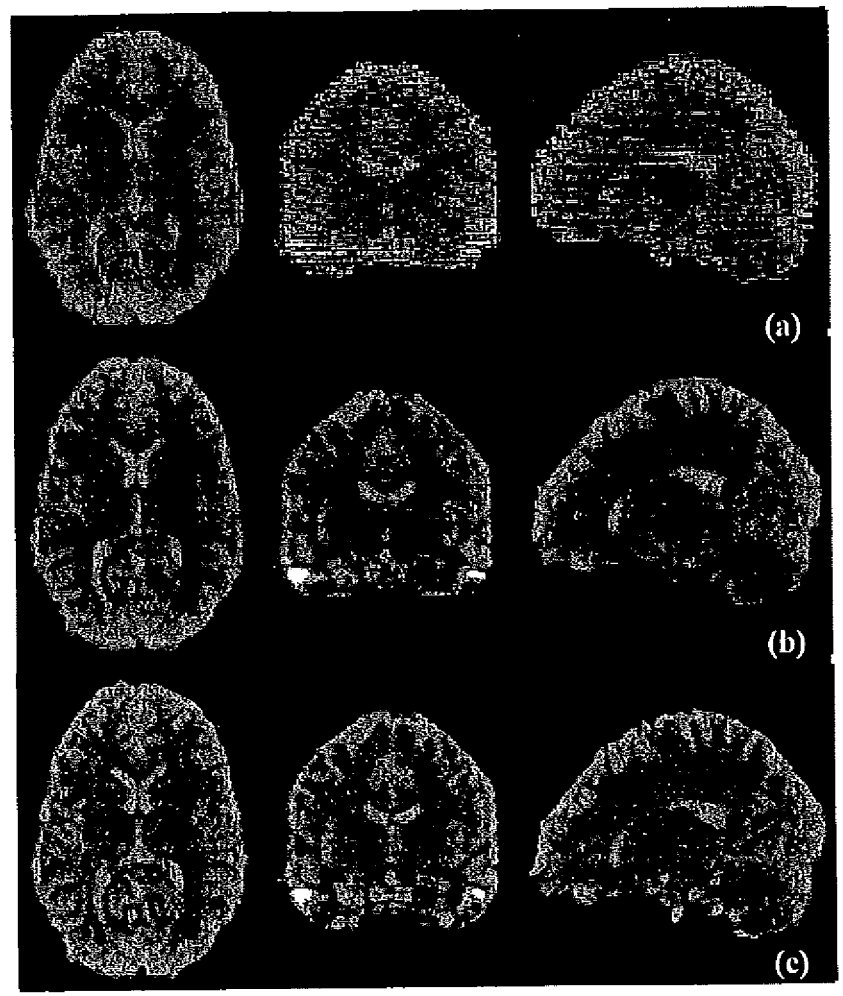
FIG. 1 shows results for an adult volunteer that deliberately moved during scanning: b=0 image, (a) is one loop of acquired transverse b=0 slices viewed in transverse, coronal and sagittal planes with 3 mm*3 mm in-plane resolution, 3.6 mm slice thickness and −1.8 mm slice gap. (b) are the corresponding views reconstructed to a 3 mm*3 mm*1.8 mm resolution image after registration. (c) are the corresponding views of the same volunteer scanned with the same protocol but stayed still. The reconstruction has successfully achieved 3D coherent b=0 volume with both high resolution and almost doubled SNR despite of totally motion corrupted input data. The absolute mean difference between the reconstructed b=0 volume and the gold standard still volume is only 6.27 with STD 21.2 given the maximum intensity 466.

Following our previous method of acquiring T2-W anatomical data, in one embodiment the invention is used for structures that can be treated as rigid bodies, changing position and orientation during the examination, but not changing in shape, size or signal properties. We shall take the brain as an exemplar of such structures. The scenario of interest involves motion that is fast enough to preclude conventional high resolution EPI that covers the entire foetal brain, but slow enough to produce individual high quality 2D images both with and without diffusion gradient (in practice a fraction of the diffusion weighted slice data is frequently damaged, so this must also be accommodated). An example is illustrated in FIG. 4a. Here the foetal brain is the rigid body and each acquired 2D diffusion weighted slices is an accurate sample of the anatomy being imaged, although successive slices do not form a consistent representation. Note that the surrounding tissues of the mother's abdomen are also changing non-rigidly in a way that is not necessarily correlated with the foetal motion. Working in the image domain it is possible to segment the anatomy of interest and separate it from the rest of the field of view. The acquired slices consist of voxels which have a measured intensity I(X,Y,Z) at prescribed positions in the scanner frame of reference, $\Omega 0(X,Y,Z)$. We now adopt a 3D Cartesian coordinate system $\Omega(x,y,z)$ fixed relative to the anatomy of interest. This coordinate frame is moving relative to the scanner coordinate frame. The acquired voxel data are legitimate samples in $\Omega$, but at unknown locations (x,y,z). Because of the motion, the samples I(x,y,z) are irregularly spaced in $\Omega$. Provided their locations can be determined and the samples are sufficiently dense throughout the region of interest in $\Omega$, data interpolation can be used to generate a full representation on a regular Cartesian lattice (i,j,k) in $\Omega$. This much was also required for SVR of anatomical images. In the case of DTI data, the individual diffusion weighted slices have different contrast both relative to the b=0 images and to each other because of the effects of varying the direction of sensitization on anisotropic tissues such as white matter tracts. This places requirements on the registration algorithm used to find the correct slice locations in $\Omega 0$. In addition the correct sensitization direction for each acquired slice must be maintained once it is correctly placed in the anatomical space. Successful reconstruction of a 3D representation of diffusion tensor matrix that can then be reformatted into any desired plane thus has 3 requirements:

1) Sufficient samples in $\Omega$ to allow full representations of the structure that contains at least 6 independent diffusion directions as well as a non-diffusion (b=0).

2) Determination of the mapping from $\Omega_0(X,Y,Z)$ to $\Omega(x,y,z)$ for each sample 3) Reconstruction of the diffusion tensor matrix D on a regular sampled 3D space given the scattered, irregularly spaced samples I(x,y,z) that are each associated with an appropriately oriented diffusion gradient direction.

Achieving the Required Sample Density

We first consider the case of a static brain imaged with 2D slices. Within the individual slice plane the data is acquired in the Fourier domain with k-space sampled at the Nyquist spacing for the desired field of view up to a maximum value that sets the in plane resolution. The images are strictly bandlimited. In the through slice direction the point spread function (PSF) is the slice profile, which is approximately Gaussian for the single shot sequences used. Following Noll (12) and our previous discussion in (3), sampling at intervals of about half the full width at half maximum (FWHM) of the slice profile is required. We therefore adopt a strategy of imaging with slices separated by H=0.5 FWHM. It is then logical to regard H as the nominal resolution length used for reconstruction in the slice direction.

Since the objective is to produce a 3D image volume we choose imaging parameters that result in approximately isotropic resolution. Neglecting effects of T2* decay during the EPI readout, the acquired in-plane PSF is a Sin c function which has FWHM of the central peak equal to 1.2 times the acquired pixel resolution (L) and the first zero crossings are separated by 2 L. Ideally, to achieve isotropical 3D PSF in both in-plane and through slice direction, the slice separation H should be set as 0.6 L and the slice thickness is 2 H. However, thin slice thickness will result in low SNR especially when the diffusion sensitization gradient is on. On balance, in what follows we generally set H=0.75 L-L depending on the maturity of foetal brain. The less mature the foetal brain is, the thinner the slice thickness is set. Thus the 3D PSF is anisotropic with a central peak that is slightly narrower in the in-plane direction, but is more localized in the slice selection direction. The sampling strategy ensures full sampling in all 3 dimensions and the effective maximum spectral content is approximately equal in all directions, although the k-space filtering is likely to be more pronounced in the slice select direction.

Although only 6 independent diffusion directions are required to reconstruct the symmetric diffusion tensor matrix D, it is well known that using more non-collinear diffusion directions increases the accuracy of diffusion tensor fitting (13). Moreover, as suggested by Chang (14), increasing diffusion gradient directions will lead to more robust tensor fitting than using the minimum 6 diffusion gradient directions only while repeating the whole set of acquisition several times. Therefore, 15 diffusion directions is adopted in this embodiment.

In the proposed application the brain to be imaged may move between individual slice acquisitions. This causes uneven slice samples when viewed in the anatomical reference frame ($\Omega$) and is likely to result in violation of the Nyquist sampling criterion at some locations. To avoid this problem the target volume in $\Omega_0$ is repeatedly imaged by simply looping through all slice positions so that in the absence of motion each location under different diffusion gradients is sampled multiple times. We refer to each complete set of slices spanning $\Omega_0$ for the entire set of diffusion weighted images-under different diffusion gradient direction plus one non diffusion weighted image as a loop. The number of loops required depends on the motion. In these experiments we used 3-4 loops each with 15 non-linear diffusion directions subject to the acceptability of the patients.

Determine the Mapping from $\Omega_0$(X,Y,Z) to $\Omega$(x,y,z) for Each Sample

A self consistent 3D b=0 image V0 is first reconstructed using method described in (1-3). Then, motion correction to determine the transformation that maps from laboratory coordinates $\Omega_0$(X,Y,Z) to anatomy coordinates $\Omega$(x,y,z) for each diffusion weighted slice is preformed by registering each of them to the b=0 volume in a multi-time scale hierarchical way with normalized mutual information (NMI) as the cost function.

The data is first divided into temporally contiguous blocks each containing multiple slices that together provide full coverage of the volume of $\Omega_0$(X,Y,Z) of interest for one respective diffusion direction (i.e. 1 stack of either no diffusion or diffusion weighted image from each loop). Neglecting subject motion, these slice blocks are treated as 3D volumes and registered to the 3D b=0 volume V0 using rigid body transformations.

Once the data is aligned, the time scale is then reduced so the data is divided into sub-packages that are temporally contiguous although the slices in each sub-package may not be spatially contiguous. These sub-packages are each registered to V0. The registration process involves moving the sub-package with V0 held fixed in space. When the transformations (T($\Omega 0 \rightarrow \Omega$)) of all sub-packages have been determined, the time scale is then reduced again and the process repeated until each slice is treated in isolation.

The method requires individual 2D slices to be registered to a 3D volume. This is a difficult problem; particularly in the premature brain which has less complex patterns of sulcation than adult brains. Accordingly a brute force search, the slice/stack-to-volume registration method was developed based on a multi-start, multi-resolution approach using the Powell method to optimize each transformation parameter in turn (see ref. 3). When registering non diffusion weighted slices to its corresponding volume, cross correlation is chosen as an appropriate cost function (see ref. 15) because the data has consistent contrast properties. When registering diffusion weighted slices to the b=0 volume, normalized mutual information is used because of different contrast types associated with diffusion weighted images with different diffusion gradient direction.

For the foetal data registration, the initial range of angles tested was typically −18 to 18 degrees of rotation in all three directions to ensure that the possible motion of the foetus is covered. In later stages, finer ranges of rotation can be accepted to accelerate registration, as the starting estimate is known with increasing confidence. We used −9 to 9 degree of rotations for the second stage, −6 to 6 degree rotations for the third and −4 to 4 degree rotations for the fourth. At the final single slice stage, −2 to 2 degree rotations are used. Cubic Bspline interpolation is used at the final registration stage, while at the previous stages, trilinear interpolation is used.

Reconstruction of the Diffusion Tensor Matrix in Anatomical Space on a Regular Grid Using an anatomic coordinate system fixed relative to the reconstructed b=0 image volume V0, and given acquired diffusion sensitization direction g, rotation matrix R with respect to V0, and the corresponding intensity $I_0$ in V0 determined via cubic Bspline interpolation, the measured diffusion intensity I can be determined by:

$$I = I_0 * \exp(-bg'D_{Lob}g) = I_0 * \exp(-bg'(R'D_{\lambda na}R)g) \quad (1)$$

$D_{Lob}$ and $D_{\lambda na}$ are the diffusion tensor matrix in laboratory and anatomic coordinates respectively. We can further convert the measured diffusion intensities to normalized logarithm values S using equation (2) to prepare for later linear tensor fitting.

$$s = -\log(I/I_o)/b = g'(R'D_{\lambda na}R)g \quad (2)$$

Once aligned, we treat the data set s as a whole as irregularly sampled with each voxel associated with an appropriately rotated diffusion direction, and use all the data to estimate the diffusion tensor D on a regular grid. For each scattered point $s_{scatter}$, we can use equation (3) to define its value, where the $\beta_i$ are spatial coefficients associated with the diffusion tensor matrix $D_{\lambda na;regular,i}$ on the regular grids. $D_{\lambda na,scatter}$ is the diffusion tensor matrix associated with $s_{scatter}$ in anatomy coordinate.

$$s_{scatter} = g'(R'D_{\lambda na,scatter}R)g = \Sigma_{i=1}^{N}\beta_i g'(R'D_{\lambda na;regular,i}R)g \quad (3)$$

We can then reconstruct the scattered diffusion tensor to a regular grid by solving a huge matrix equation, (4), $$\bar{s}_{scatter} = M_R M_G * \mathrm{diag}(M_S, M_S, M_S, M_S, M_S, M_S) * [D_{xx}; D_{yy}; D_{zz}; D_{xy}; D_{xz}; D_{yz}] \quad (4)$$

where $\bar{S}_{scatter}$ is a vector containing values of measured intensity at all the scattered points, $M_R$ is a matrix specifying rotations R, $M_G$ contains the diffusion gradient directions and $M_S$ is a spatial interpolation matrix. They are all sparse. $D_{xx}$–$D_{yz}$ are 6 independent parameters of the diffusion tensor. We use the Sparse Equations and Least SQuares Regression (LSQR) method (see ref. 11) to solve for sparse matrix $D_{xx}$–$D_{yz}$, and then calculate its eigenvalues to determine corresponding ADC and FA values. Nearest Neighbor interpolation is used here to estimate the spatial coefficient $\beta_i$ given dense sampling.

The 3×3 symmetric diffusion tensor matrix D should be positive definite, i.e., all the three eigenvalues should be strictly positive. A further refinement using constraint minimization is performed to guarantee the positive definition of the diffusion matrix. This is achieved by reformatted the diffusion matrix with 3 eigenvalues together with 3 rotations to define its principle eigenvector, and then performing a second least squares fit while constraining all eigenvalues to be positive.

Foetal Subjects and Scanning Protocol

Foetal brain images were acquired on a 1.5 T Philips Achieva scanner (Best, The Netherlands) using a 5 channel torso array with a spin echo echo planar diffusion tensor sequence. Image matrix of 150×150, field of view of 300 mm (acquired resolution 2 mm×2 mm) and slice thickness 3 to 4 mm with half slice thickness, i.e., −1.5 to −2 mm gap were used depending on the maturity of the foetus. 72 slices are used to cover the entire region of foetal brain. Slices were acquired in 2 packages and within each packages starting at one extreme end in an interleaved order, i.e., 1, 5, 9, . . . 3, . . . , 2, 6, 10, . . . , 4, . . . to avoid slice cross-talk by ensuring that for each slice the previously excited closest slices were separated by 4 H and sequentially acquired. We set the repeat time TR to be 12 s for each package to avoid spin history effects while TE is chosen to be the shortest possible (54 ms) given b-value 500 s/mm2. The mother was free breathing during scanning and no sedation was used. Although parallel imaging methods (e.g. SENSE (see ref. 16)) can be a powerful addition to many EPI based studies, we found that changes in maternal position during free breathing foetal examination frequently resulted in reconstruction artifacts caused by a mismatch between the varying coil position and the previously acquired reference data. The EPI factor is 149 without any parallel imaging acceleration. In this study parallel imaging was not applied. Typical scanning time was 7 minutes for 15 diffusion directions. In addition test data was obtained from adult volunteers who either lay still or deliberately moved their head.

Eight foetuses were examined with gestational age between 24 and 34 weeks. Two were diagnosed from Ultrasound and conventional foetal MRI as normal while two had mild ventricular dilation, two had agenesis of the corpus callosum, one had mild unilateral ventricular dilation and one had destructive process possibly caused by a virus.

The foetal brain images were pre-processed to isolate the region containing the head from the womb using a Semi-automated segmentation method. We first segment one loop of the foetal brain by roughly tracing the edge of the head manually to exclude maternal tissues. For a foetal data set consisting of 72 slices, the whole process takes around 20 minutes using ImageJ[1]. The foetal brain is then extracted from all the other images using a registration based segmentation [B3]. This segmentation is later refined by interleaving it with the registration process used to determine slice alignment, allowing both registration and segmentation to be iteratively improved. All slices were inspected and the slices that were corrupted by in-plane motion were excluded before registration and reconstruction.

A high resolution anatomical volume acquired with T2-W single short Turbo Spin Echo (ssTSE) dynamic sequence as described in SVR (see ref. 3) was also reconstructed for comparison. They have 1.25 mm×1.25 mm in-plane resolution, 2.5 mm slice thickness and −1.25 mm slice gap, with TE=110 ms, TR=1000 ms and SENSE factor 2.

Test Data for Registration and Reconstruction Accuracy

Images of adult brains acquired with spin echo EPI were used to test the accuracy of slice-to-volume registration for diffusion data and the subsequent reconstruction. Two datasets were acquired using the same diffusion tensor imaging protocol at 1.5 T but with a SENSE head coil. In one examination the subject remained as still as possible and four different sets of DTI data with 15 non-collinear directions were acquired in a transverse orientation with in-plane resolution 3 mm×3 mm, slice thickness 3.6 mm and −1.8 mm slice gap. To closely simulate the foetal protocol, SENSE was not used and TR was 8 seconds while TE was 55 ms which was the minimum for a b value 500 s/mm$^2$. Each image set was angulated away from its standard plane by varying amounts up to 30 degrees to simulate the effects of variations in head position that would be caused by motion. One b=0 stack out of these 4 was chosen as the target volume. Every fourth slice from the other stacks including both b=0 and diffusion weighted images with different diffusion gradient directions, i.e., 819 slice's from 63 stacks in total, was extracted and treated in isolation, providing equally spaced example slices that covered the majority of the brain. Each of the individual slices was registered to the target volume using slice-to-volume registration.

In a second set of experiments an adult volunteer deliberately moved about once per second, including making head rotations up to 30 degree. Four loops of 15 direction DTI data were acquired. The protocol was identical to that used in the previous test. For comparison, images were also acquired with the same protocol while the subject was still. Because of this intense motion and the high sensitivity to even small amount of motion of diffusion weighted imaging, some slice images were found to be degraded by movement during the EPI acquisition itself. All the slices that were not corrupted by in-plane motion were registered and reconstructed. The results were then compared to the gold standard (volunteer stationary) data to validate the method.

Registration accuracy for the adult data was assessed by visual comparison of the anatomy in the slices and the aligned volumes and directly compared with the gold standard volume-to-volume registration. For the moving DTI data, reconstruction fidelity was assessed visually using difference images and by calculating the mean absolute difference and its standard deviation (STD) between the gold standard and the reconstruction for b=0 volume, ADC and FA values. Moreover, Region of Interest (ROI) measurement on both ADC and FA values are also performed.

Results

Slice-to-Volume Registration Accuracy

The slice-to-volume registration algorithm correctly placed randomly selected slices into corresponding 3D volumes in all cases tested even when given no initial guess, although, a reasonable starting point allows use of a smaller search range, dramatically accelerating the optimization process. 819 slices including both b=0 and diffusion weighted images with different diffusion gradient directions were tested in total. As shown in Table 1, when tested on adult data for which a ground truth could be known, the rigid body transformation determined by 2D to 3D registration was in excellent agreement with the reference 3D to 3D registration using Image Registration Toolkit[21], which we used as a gold standard since the same 2D slices were then registered as part of 3D volumes. It was found to be accurate to 0.81 mm (STD 0.64 mm) in translation and 0.5 deg (STD 0.49 deg) in rotation, which is ¼ voxel accuracy given in-plane resolution 3 mm×3 mm and slice thickness 3.6 mm. The anatomical correspondence was confirmed by detailed visual comparison.

Adult Validation

A self-consistent 3D b=0 image volume was first reconstructed using the SVR (3) method. As displayed in FIG. 1, slice-to-volume registration has successfully corrected motion for each slice, thus the reconstructed b=0 data is almost identical to the gold standard b=0 data that was acquired when the subject stayed still. As displayed in FIG. 1, the reconstructed B0 data is almost identical to the gold standard $b_0$ data that was acquired when the subject stayed still. The standard error, i.e., the square root of the residual mean square, between the reconstructed volume and the gold standard is 3.6%. This makes an accurate target volume for registering diffusion slices.

Figure 2:
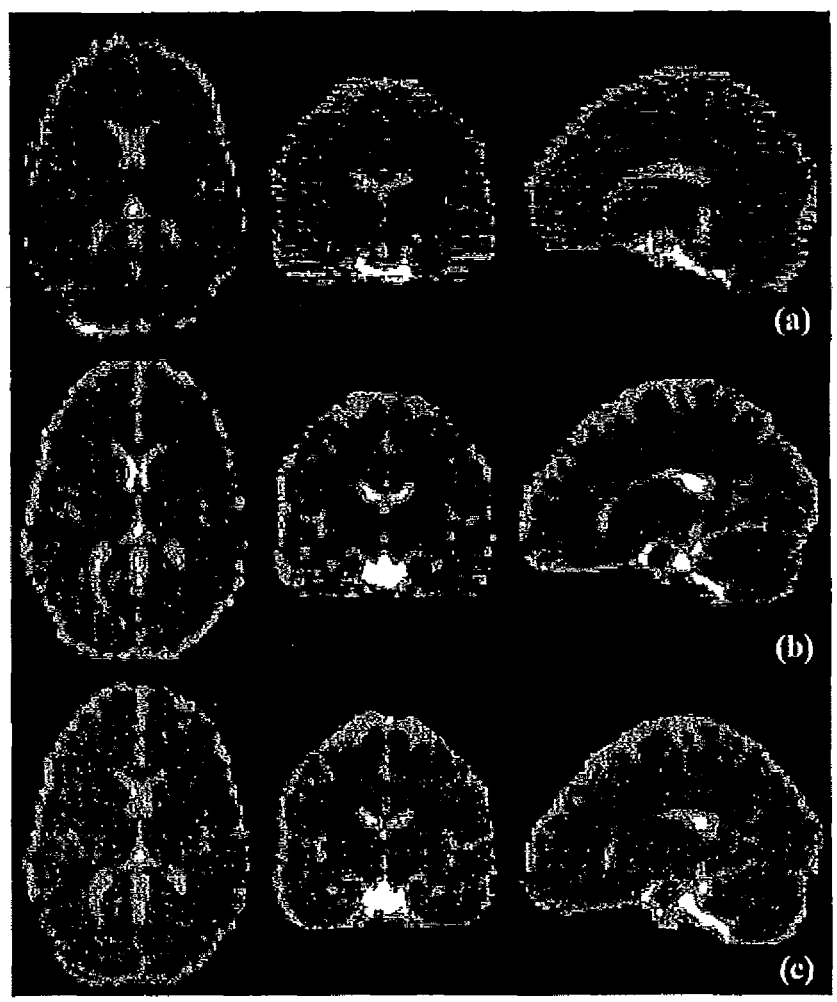
FIG. 2 shows results for an adult volunteer that deliberately moved during scanning: ADC maps. (a) is the ADC maps reconstructed directly from one set of diffusion tensor imaging with 15 directions before motion correction viewed in transverse, coronal and sagittal planes, (b) are the corresponding views of the ADC maps reconstructed to a 3 mm*3 mm*1.8 mm resolution image after registration and scattered diffusion tensor fitting. (c) are the corresponding views of the ADC maps from the gold standard volunteer stayed still data. The reconstruction has successfully achieved 3D coherent ADC maps that is almost identical with the gold standard despite of totally motion corrupted input data. The absolute mean difference in ADC values between the reconstruction and the gold standard is only 0.047 $\mu m^2$/ms with STD 0.126 $\mu m^2$/ms given the maximum ADC value 3 $\mu m^2$/ms.
Figure 3:
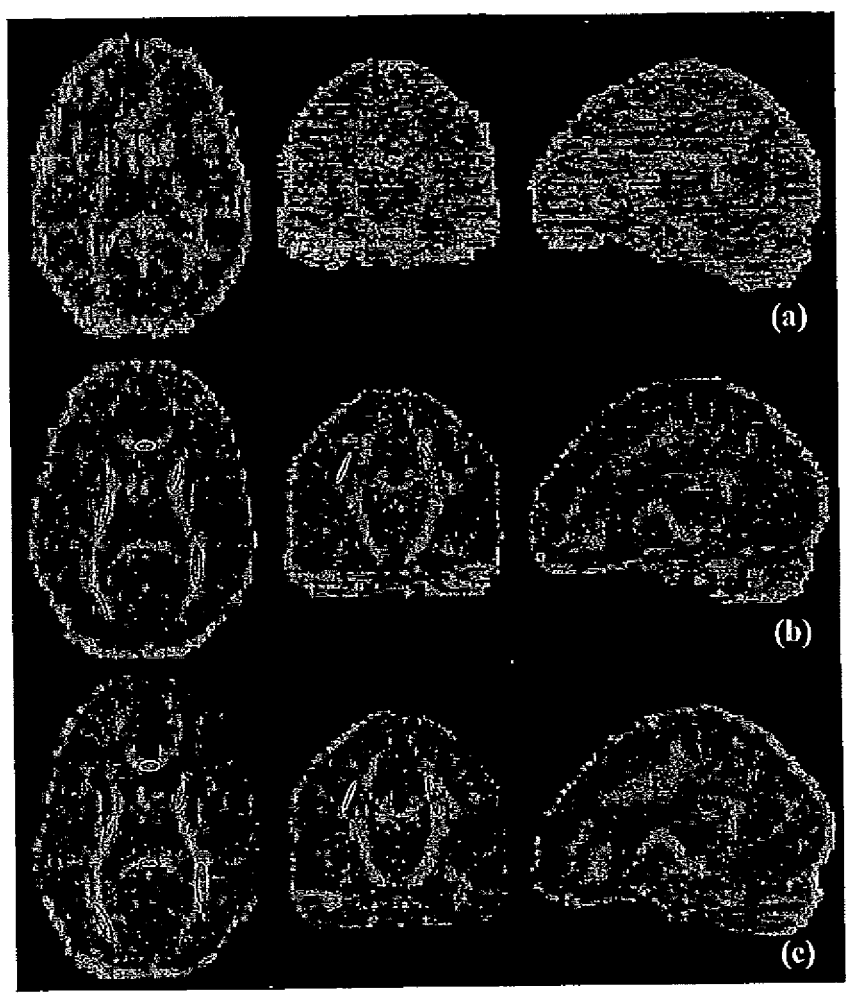
FIG. 3 shows results for adult volunteer that deliberately moved during scanning: FA maps. (a) is the FA maps reconstructed directly from one set of diffusion tensor imaging with 15 directions before motion correction viewed in transverse, coronal and sagittal planes. (b) are the corresponding views of the FA maps reconstructed to a 3 mm*3 mm*1.8 mm resolution image after registration and scattered diffusion tensor fitting. (c) are the corresponding views of the FA maps from the gold standard volunteer stayed still data. The reconstruction has successfully achieved 3D coherent ADC maps that is almost identical with the gold standard despite of totally motion corrupted input data. The absolute mean difference in FA values between the reconstruction and the gold standard is only 2.8% with STD 7.1% given the maximum FA value 100%.

After motion correction and fitting of the diffusion tensor to the resulting scattered data, the reconstructed 3D ADC map (FIG. 2(b)) shows clear consistency of ADC values. This contrasts with the corrupted ADC evaluation obtained without motion correction (FIG. 2. (c)). When compared to the gold standard ADC values of the same subject when scanned stationary, standard error of 5.6%. Because of motion, those two volumes are not perfectly aligned with each other, therefore, small amount of rotation and translation is added. The 3D FA map as displayed in FIG. 3(b) is quite close to the gold standard displayed in FIG. 3(c) as well, and found to achieve a standard error of 6.7% in FA Value. Furthermore, eight Regions of Interest (ROI) measurement including Genu of Corpus Callosum (GCCe), Splenium of Corpus Callosum (SCC), Posterior Limb of Internal Capsule (PLIC), Forceps major (FC), Anterior Limb of Internal Capsule (ALIC), Posterior region of Corona Radiate (PCR), Superior Longitudinal Fasciculus (SLF) and Superior region of Corona Radiate (SCR) on both ADC and FA values as displayed in FIG. 3(c) were performed for detailed validation. The reconstructed ADC and FA values achieved excellent agreement with the gold standard subject still data in all 8 ROIs as listed in Table 2.

Although the very bottom part of the brain is less accurate, because of a lack of data for six independent diffusion directions there, the majority of the brain has achieved accurate reconstruction.

Foetal Examples

Figure 4:
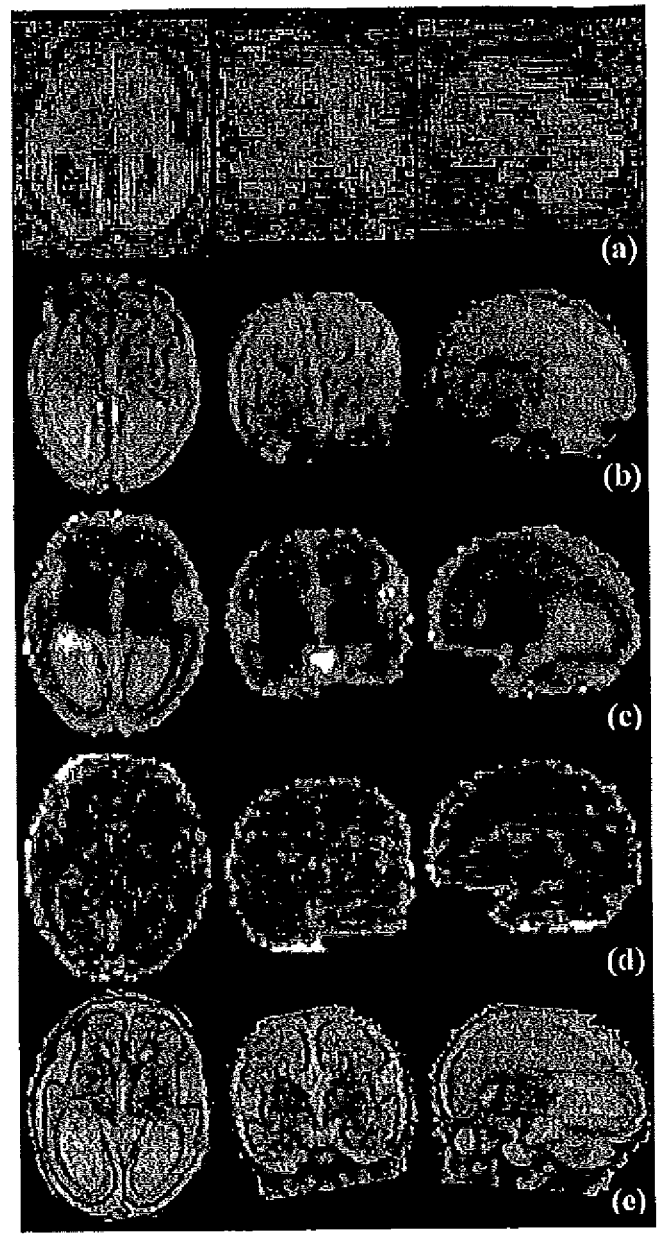
FIG. 4 shows one example of 15-direction DTI of a foetus of 26 weeks plus 5 days. (a) is one loop of acquired foetal Diffusion transverse data viewed in Transverse, Coronal and Sagittal planes with 2 mm×2 mm in plane resolution, 4 mm slice thickness and −2 mm gap. (b)-(d) are corresponding reconstructed b0 image, ADC map and FA map respectively with 2 mm×2 mm in plane resolution, and 2 mm through slice resolution. (e) is reconstructed anatomical data from a 4-loop of ssTSE dynamic scan with 1.25 mm cubic resolution.
Figure 5:
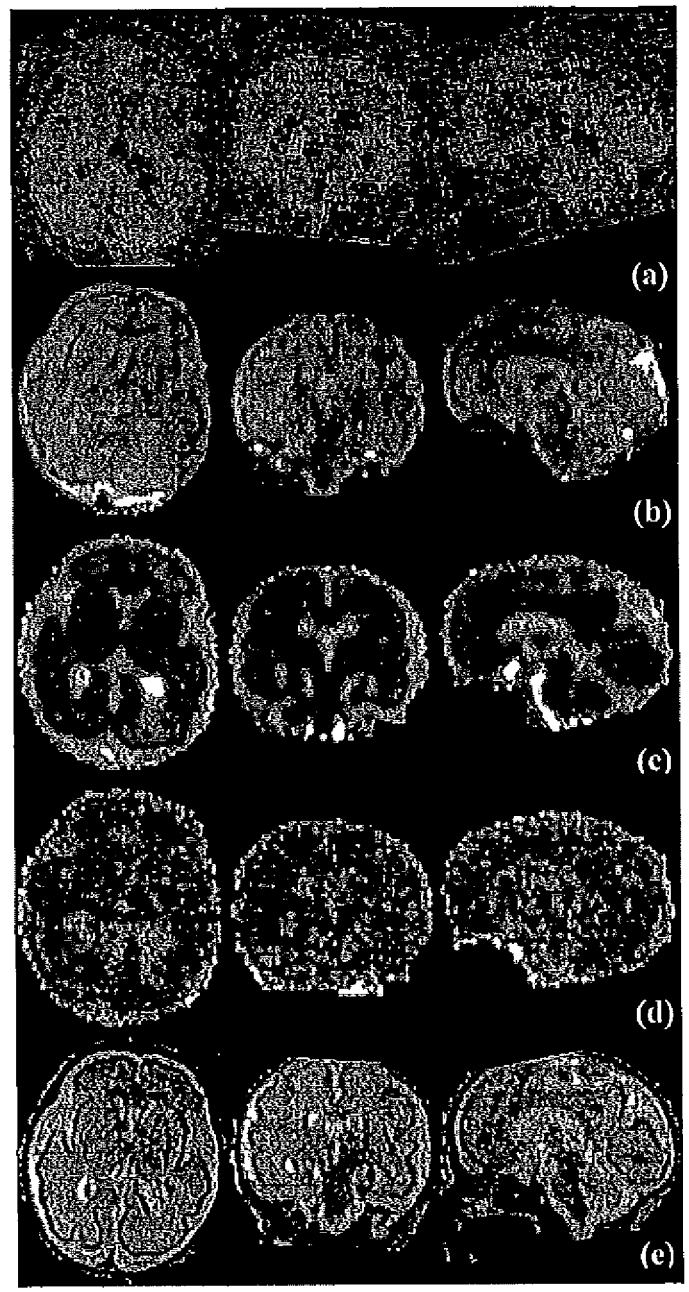
FIG. 5 shows one example of 15-direction DTI of a foetus of 30 weeks. (a) is one loop of acquired foetal Diffusion transverse data viewed in Transverse, Coronal and Sagittal planes with 2 mm×2 mm in plane resolution, 4 mm slice thickness and −2 mm gap. (b)-(d) are corresponding reconstructed b0 image, ADC map and FA map respectively with 2 mm×2 mm in plane resolution, and 2 mm through slice resolution. (e) is reconstructed anatomical data from a 4-loop of ssTSE dynamic scan with 1.25 mm cubic resolution.

The method has been tested on eight foetal subjects with 3-4 loops of 15-direction DTI scans. All have been successfully reconstructed. FIG. 4 shows data from a foetus of 26 weeks plus 5 days gestational age that had enlarged ventricles. It was scanned with 15 diffusion gradient directions, and 4 loops of transverse data were acquired with 2 mm in-plane resolution and 4 mm (2 mm slice separation) slice thickness. FIG. 5 shows data from a more mature foetus of 30 weeks gestational age. It was also scanned with 15 diffusion gradient directions, and 3 loops of transverse data were acquired with the same spatial resolution. Almost ¼ of slices were corrupted because of extreme sensitivity to motion, and so had to be excluded. The acquired slice data is not consistent in space FIG. 4(a) and FIG. 5(a). Final reconstruction achieved 2 mm isotropic resolution in all three dimensions for b=0 image, as well as ADC and FA maps. Successful reconstruction of the 3D b=0 image volume FIG. 4(b) and FIG. 5(b) makes an accurate target for registering the diffusion weighted slices. After motion correction, the reconstructed 3D ADC map FIG. 4(c) and FIG. 5(c) show clearly consistent appearances of ADC values. Different tissue types can clearly be differentiated, i.e. WM, CSF and cortex on the FA map FIG. 4(d) and FIG. 5 (d). The FA calculation is less robust than ADC and the results show greater fluctuations. A high resolution anatomical volume acquired with T2-W single short Turbo Spin Echo (ssTSE) dynamic sequence was also reconstructed for comparison in FIG. 4(e) and FIG. 5(e) with 1.25 mm cubic resolution.

ROI Analysis for ADC and FA Values

Figure 6:
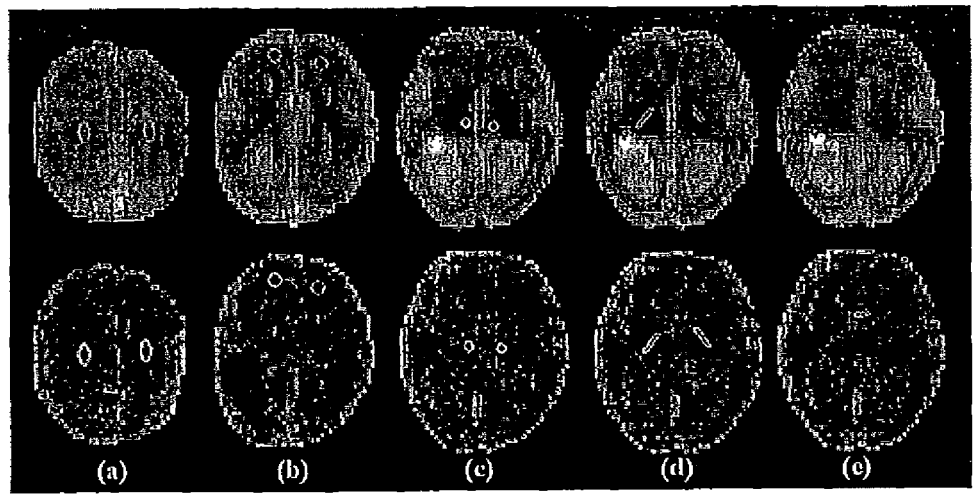
FIG. 6 shows a sampler of 5 Region of Interest (ROI) measurements on the foetal ADC and FA maps from the same foetus as displayed in FIG. 4. They include Left and Right Central Centrum Semiovale, Left and Right Frontal White Matter, Left and Right Thalamus, Left and Right Posterior Limb of Internal Capsule (PLIC) and Genu of Corpus Callosum(GCC) as displayed in (a)-(e) respectively.

Region of Interest (ROI) analysis was performed on all foetal subjects. ADC measurements could be made for all 8 subjects, while 5 of them had FA maps of sufficient quality for measurement. FIG. 6 shows the locations of the sampled regions which included the Left and Right Central Centrum Semiovale (Lt/Rt central CSO), Left and Right Frontal White Matter (Lt/Rt FrontalWM), Left and Right Thalamus (Lt/Rt Thalamus), Left and Right Posterior Limb of Internal Capsule (Lt/Rt PLIC) and Genu of Corpus Callosum (Genu). The measured values obtained for each subject are listed in Table 3 and 4. Measurements were also made in the splenium of the corpus callosum of 4 subjects when this was clearly visible.

ADC values depend on water content which is known to decrease with increasing gestational age but also with the cellular content of the tissue. Immature white matter contains bands of migrating cells which may modulate the ADC as they migrate through the hemispheres, possibly disrupting simple direct relationship between gestational age and ADC values. Anisotropy increases in white matter with increasing gestational age resulting in increasing FA values. However, in preterm newborns with white matter injury, these maturational trends in FA may be diminished or even reversed (17). The ADC and FA values of our foetal data especially the normal ones are in consistency with the corresponding ex-utero measurements published in (17).

It will be appreciated that the methods described above can be performed using a conventional scanner and any suitable processor for processing the data. Typically the processor will form part of a computer which also includes a display on which the image, generated from the scan data, can be displayed. However, rather than being displayed, the scan data may be analysed using suitable algorithms.

DISCUSSION AND CONCLUSION

We have described in this embodiment a novel methodology for perform diffusion tensor imaging on moving subjects by combining registered 2D slices from sequential diffusion weighted scans. The method requires that the anatomy in question is not changing shape or size or diffusion properties and is moving at a rate that allows EPI images to be acquired. It has been performed successfully on adults and especially on foetuses, for which no conventional diffusion tensor imaging method is currently available. Fine structure on both ADC and FA map indicating microstructural development of the in-utero foetal brain is clearly revealed for the first time. The registration process was found to be robust in the presence of noise, so that thinner higher resolution slice data can be used without loss of accuracy in the position estimation.

The other key feature of the method is diffusion tensor matrix reconstruction to combine scattered data from realigned slices into a regular grid for the final reconstructed images. The data may contain samples that are spatially very close together, and because these may come from separately acquired slices, they are subject to uncorrelated noise as well as different diffusion gradient directions. This places a duel requirement on the accuracy of registration; correct alignment of samples in the anatomical space and correct prescription for the direction of diffusion sensitization in anatomical space. The FA calculation places particular emphasis on this combined need and the fact that the results proved to be both plausible anatomically and numerically consistent in magnitude provides support for the conclusion that sufficient precision has been achieved. The internal consistency of the adult test data provides further supporting evidence.

Following ref 18, the signal intensity ρ for single shot spin echo EPI will be determined by Equation (5)

$$\rho = \rho_0 e^{-T_E/T_2*}(1-e^{-T_R/T_1}) \qquad (5)$$

$\rho_0$ is the effective spin density, $T_E$ is the echo time, $T_R$ is the repeat time. $T_R$ should be at least 3 time of spin-lattice relaxation time $T_1$ to guarantee the fully recover of longitudinal magnetization to prevent any signal loss. It is well understood that the neonatal brain has higher water content (92%-95%) than the adult brain (82%-85%), and so the $T_1$ of neonate is greater (19). These values decrease with increasing age, and adult values are reached in early childhood. The $T_1$ of the foetal CSF at 1.5 T is assumed to be as long as it of the distilled water, i.e. 4 s, therefore, $T_R$ is set to be 12 second. Although less efficient because of the long $T_R$, our experiment shows shorter $T_R$ than that will have residual spin history effect, i.e. there is intensity modulation between adjacent slices that belongs to different packages. Beside, Longer $T_R$ will also improve the signal-to-noise ratio (SNR), which is especially beneficial for in-utero foetal DTI.

As mentioned before, parallel imaging techniques that rely on pre-acquired reference data is not used in in-utero foetal DTI because of the mother changing her position that leads to a mismatch between the varying coil position and the previously acquired reference data. However, this will increase the total number of phase encoding for each 2D slice, and thus increase $T_E$ that result in reduced SNR. Moreover, collecting data over a long sampling time will cause the term $e^{31\ T_E/T_2*}$ to significantly modulate the signal amplitude. As illustrated in ref 17, the blur or extra effect on spatial resolution is in direct ratio to the number of phase encoding. And this may limit the achievable actual in-plane resolution of foetal DTI, although we haven't found any noticeable resolution loss at 2 mm×2 mm.

In general, as shown in FIG. 4 and FIG. 5(a), the diffusion weighted images of in-utero foetal brain have much poorer SNR compared to those of adult or neonatal brain imaged with SENSE head coil. When imaging postnatal brain, the patient can often manage to stay still during scanning, or sedation is used for neonatal scan. Therefore, parallel imaging techniques, e.g. SENSE can be used to accelerate the scanning, and reduce the EPI factor. Moreover, for postnatal scanning the total FOV can be set just enough to cover the entire brain, i.e. 230 mm, while for the foetal scanning the FOV should be enlarged to 300 mm to cover the maternal abdomen, which will also increase the phase encoding steps, i.e. the EPI factor. Thus $T_E$ of postnatal brain DTI can set to be much shorter to achieve higher SNR as well as reduced $T_2*$ effect resulting in minimum resolution loss. Furthermore, in some cases, the foetal brain is embedded deeply in the womb that is far away from the torso coil. This will also result in signal loss because the sensitivity of this kind of surface coil will decrease with increasing distance.

Geometrical distortion is also a much less severe a problem because B0 homogeneous is improved largely in the in-utero environment, where only minimum air-tissue interfaces exist. Moreover, shimming over small region containing foetal brain only, e.g. 100 mm cubic volume will be more effective.

The price of the benefits offered by this technique is increased scan time to allow multiple loops to be acquired. In the case of foetal scanning, since no breath hold or sedation is required, this has been found to be easily tolerated by the subjects scanned so far. For adult and pediatric subjects the method offers a capability to obtain high quality diffusion tensor reconstruction even when the subject is unable to cooperate with the examination and may be moving by many millimeters or turning by many degrees during the acquisition period. Validation using adult data has been performed to verify that the results obtained are consistent with the known ground truth and the reconstruction faithful.

The capability to observe the foetal brain in-utero using both anatomical images and diffusion tensor images of high resolution and high contrast provides a new opportunity to study the developing human brain and will allow direct comparison between pre-term and post partum brains for the first time. This is likely not only to be a very valuable clinical tool, but it will also empower studies employing volumetric, morphometric and tractographical approaches that may lead to new insights into the process of human brain development. It will also allow detailed comparison between foetuses and preterm neonates at the same gestational age imaged with the same sequences and processed in the same way. This may be an essential tool for further understanding the effects of prematurity on brain development.

In summary this method provides a robust technique for performing diffusion tensor imaging on moving structures that behave as rigid bodies and so do not change size or shape. Brain imaging in uncooperative subjects is a clear application with foetal imaging as a particularly exciting exemplar. It may also be feasible to extend the method to work with less constrained realignment strategies, such as to allow correction of slice distortion. An appealing feature of the method is that it can readily accommodate scenarios where there is differential change within the field of view. In these kinds of applications efficient segmentation methods as well as selecting motion corrupted slices will be required to avoid extensive manual intervention in what is otherwise a completely automatic process.

Figure 7:
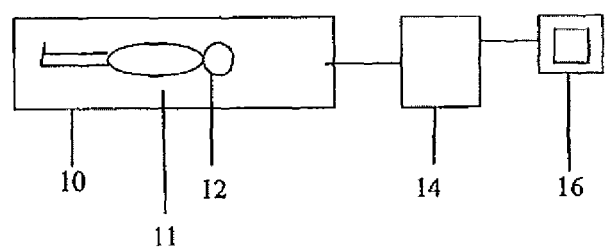
FIG. 7 is a schematic diagram of a system according to an embodiment of the invention.

Referring to FIG. 7, in one embodiment of the system according to the invention, a scanner 10 has a scanning space 11 in which a subject 12 can be placed to perform a scan. A processing system 14 is arranged to receive scan data in the form of sample sets from the scanner, to process the sample sets, and produce an image on a display 16. While the processing system 14 is shown as connected to the scanner 10, this does not always need to be the case, and the processor can receive the sample sets indirectly from the scanner.

REFERENCES

1. Jiang S, Xue H, Glover A, Rutherford M, Rueckert D, Hajnal J V. A novel approach to accurate 3D high resolution and high SNR fetal brain imaging. ISBI 2006: 662-665.
2. Jiang S, Xue H, Glover A, Rutherford M, Rueckert D, Hajnal J V. A novel approach to accurate 3D high resolution and high SNR fetal brain imaging. ISMRM 06: 731.
3. Jiang S, Xue H, Glover A, Rutherford M, Rueckert D, Hajnal J V. MRI of moving subjects using multi-slice Snapshotimages with Volume Reconstruction (SVR): application to fetal, neonatal and adult brain studies. Medical Imaging, IEEE Transactions on 2007.

4. Baldoli C, Righini A, Parazzini C, Scotti G, Triulzi F. Demonstration of acute ischemic lesions in the fetal brain by diffusion magnetic resonance imaging. Ann Neurol 2002; 52(2):243-246.
5. Righini A, Bianchini E, Parazzini C, Gementi P, Ramenghi L, Baldoli C, Nicolini U, Mosca F, Triulzi F. Apparent diffusion coefficient determination in normal fetal brain: a prenatal MR imaging study. AJNR Am J Neuroradiol 2003; 24(5):799-804.
6. Prayer D, Kasprian G, Krampl E, Ulm B, Witzani L, Prayer L, Brugger P C. MRI of normal fetal brain development. Eur J Radiol 2006; 57(2):199-216.
7. Moseley M. Diffusion tensor imaging and aging—a review. NMR Biomed 2002; 15(7-8):553-560.
8. Counsell S J, Boardman J P, Differential brain growth in the infant born preterm: current knowledge and future developments from brain imaging, Semin Fetal Neonatal Med 2005; 10(5):403-410.
9. Rutherford M, Counsell S, Allsop J, Boardman J, Kapellou O, Larkman D, Hajnal J, Edwards D, Cowan F. Diffusion-weighted magnetic resonance imaging in term perinatal brain injury: a comparison with site of lesion and time from birth. Pediatrics 2004; 114(4):1004-1014.
10. Bui T, Daire J L, Chalard F, Zaccaria I, Alberti C, Elmaleh M, Garel C, Luton D, Blanc N, Sebag G. Microstructural development of human brain assessed in utero by diffusion tensor imaging. Pediatr Radiol 2006; 36(11):1133-1140.
11. Paige C C, Saunders M A, LSQR: An Algorithm for Sparse Linear Equations and Sparse Least Squares. ACM Transactions on Mathematical Software (TOMS) 1982; 8(1):43-71.
12. Noll D C, Boada F E, Eddy W F. A spectral approach to analyzing slice selection in planar imaging: optimization for through-plane interpolation. Magn Reson Med 1997; 38(1):151-160.
13. Basser P J, Mattiello J, LeBihan D. Estimation of the effective self-diffusion tensor from the NMR spin echo. J Magn Reson B 1994; 103(3):247-254.
14. Chang L C, Jones D K, Pierpaoli C. RESTORE: robust estimation of tensors by outlier rejection. Magn Reson Med 2005; 53(5):1088-1095.
15. Jenkinson M, Bannister P, Brady M, Smith S. Improved optimization for the robust and accurate linear registration and motion correction of brain images. Neuroimage 2002; 17(2):825-841.
16. Pruessmann K P, Weiger M, Scheidegger M B, Boesiger P. SENSE: sensitivity encoding for fast MRI. Magn Reson Med 1999; 42(5):952-962.
17. Partridge S C, Mukherjee P, Henry R G, Miller S P, Berman J I, Jin H, Lu Y, Glenn O A, Ferriero D M, Barkovich A J, Vigneron D B. Diffusion tensor imaging: serial quantitation of white matter tract maturity in premature newborns. Neuroimage 2004; 22(3):1302-1314.
18. Haacke M, Brown R, Thompson M, Venkatesan R. Magnetic Resonance Imaging, Physical Principles and Sequence Design. Wiley-Liss; 1999.
19. Tortori-Donati P, Rossi A. Pediatric Neuroradiology Brain. Springer; 2005.

The invention claimed is:

1. A method of generating an image data set describing an object, as the object moves in a scanning space relative to a scanner, the method comprising:
a) performing a plurality of scans of the scanning space to obtain sample values of each of a plurality of sampled parameters, each of the scans being arranged to generate a sample set comprising a plurality of the sample values; wherein each of the sampled parameters relates to a plurality of different parameters of the object;
b) registering the sample sets from the scanning space with a reference data set defining a 3D volume in an object space which is fixed relative to the object to form a scattered data set which comprises sample values mapped to scattered points in the object space, thereby correcting for motion of the object in the scanning space; and
c) determining object space values for each of the parameters of the object at each of a plurality of points in the object space from the scattered data set.

2. A method according to claim 1 wherein the points in the object space are arranged in a regular grid.

3. A method according to claim 1 wherein the object space values are determined by interpolation from the samples.

4. A method according to claim 1 wherein each of the sample parameters has a control parameter or state parameter associated with it.

5. A method according to claim 1 wherein each of the object space values has a direction associated with it and the mapping includes a rotation.

6. A method according to claim 1 wherein the scans are MRI scans.

7. A method according to claim 6 wherein the sample parameters include measurements of diffusion in a plurality of directions.

8. A method according to claim 1 wherein each of the scans is arranged to scan a plurality of slices of the scanner space, and each of the sample sets comprises a plurality of sample slices each sample slice comprising a plurality of the samples and being associated with one of the slices of the scanner space.

9. A method of generating an image of an object, the method comprising generating an image data set according to the method of claim 1 and generating an image from the data set.

10. A system for producing an image data set describing an object as the object moves in a scanning space relative to a scanner, the system comprising an input arranged to receive a plurality of sets of sample values including sample values of a plurality of different sampled parameters, each of the sampled parameters relating to a plurality of different parameters of the object; and processing means arranged to: registering the sample sets from the scanning space with a reference data set defining a 3D volume in an object space which is fixed relative to the object to form a scattered data set which comprises sample values mapped to scattered points in the object space, thereby correcting for motion of the object in the scanning space wherein the object space values are determined from the scattered data set.

11. A system for producing an image comprising a system according to claim 10 and a display, wherein the processing means is arranged to control the display to produce a display from the image data set.

12. A system according to claim 10 further comprising a scanner arranged to generate the sets of sample data.

13. A data carrier carrying non-transitory data arranged when run on a computer to make it perform the method of claim 1.

14. A method according to claim 1 wherein the different sampled parameters comprise different pixel intensity values for the same pixel when the object is in different states.

15. A method according to claim 1 wherein the step of registering the sample sets from the scanning space with a reference data set generates a mapping of each of the samples from the scanning space into the object space, and the step of determining the object space values comprises a linear process using all of the sampled values and the mapping.

\* \* \* \* \*